United States Patent
Li et al.

(10) Patent No.: US 11,717,351 B2
(45) Date of Patent: Aug. 8, 2023

(54) NAVIGATION SURGICAL SYSTEM, REGISTRATION METHOD THEREOF AND ELECTRONIC DEVICE

(71) Applicant: Suzhou MicroPort Orthobot Co., Ltd., Jiangsu (CN)

(72) Inventors: Tao Li, Jiangsu (CN); Chao He, Jiangsu (CN); Wuchao Cheng, Jiangsu (CN)

(73) Assignee: SUZHOU MICROPORT ORTHOBOT CO., LTD., Jiangsu (CN)

( * ) Notice: Subject to any disclaimer, the term of this patent is extended or adjusted under 35 U.S.C. 154(b) by 522 days.

(21) Appl. No.: 16/836,015

(22) Filed: Mar. 31, 2020

(65) Prior Publication Data

US 2021/0169582 A1    Jun. 10, 2021

(30) Foreign Application Priority Data

Dec. 9, 2019    (CN) .......................... 201911252494.1

(51) Int. Cl.
  *A61B 34/20*    (2016.01)
  *A61B 34/37*    (2016.01)
  (Continued)

(52) U.S. Cl.
  CPC ............. *A61B 34/20* (2016.02); *A61B 34/37* (2016.02); *A61B 34/70* (2016.02); *A61B 90/50* (2016.02); *A61B 2560/0437* (2013.01)

(58) Field of Classification Search
  None
  See application file for complete search history.

(56) References Cited

U.S. PATENT DOCUMENTS 10,993,772 B2 * 5/2021 Itkowitz ................. A61B 34/25
2016/0256223 A1   9/2016 Haimerl et al.
(Continued)

FOREIGN PATENT DOCUMENTS

CN    1243690 A    2/2000
CN    101073528 A    11/2007
(Continued)

*Primary Examiner* — Tamara L Weber
(74) *Attorney, Agent, or Firm* — Muncy, Geissler, Olds & Lowe, P.C.

(57) ABSTRACT

A navigation surgical system, a registration method thereof and an electronic device are disclosed. The navigation surgical system includes a robotic system and a navigation system communicatively connected to the robotic system; the robotic system includes a robotic arm, the navigation system includes a navigation tracking device; the robotic system has a robotic-arm based coordinate system established according to the robotic arm, and the robotic-arm based coordinate system is fixed relative to a supporting device; the navigation system has a reference coordinate system that is recognizable by the navigation tracking device, the reference coordinate system is fixed relative to the supporting device; the navigation surgical system is configured to determine a relative position between the robotic arm and the navigation tracking device according to a relative position between the robotic-arm based coordinate system and the supporting device, and a relative position between the reference coordinate system and the supporting device.

14 Claims, 5 Drawing Sheets

(51) Int. Cl.
*A61B 34/00* (2016.01)
*A61B 90/50* (2016.01)

(56) References Cited

U.S. PATENT DOCUMENTS

| | | | |
|---|---|---|---|
| 2016/0361128 A1 | 12/2016 | Seeber | |
| 2017/0079730 A1* | 3/2017 | Azizian | ................ A61G 13/02 |
| 2018/0271732 A1 | 9/2018 | Yano et al. | |
| 2018/0289427 A1* | 10/2018 | Griffiths | ................ A61G 13/10 |
| 2019/0380794 A1* | 12/2019 | Al Jewad | ................ A61B 34/20 |

FOREIGN PATENT DOCUMENTS

| | | | |
|---|---|---|---|
| CN | 104083217 A | 10/2014 | |
| CN | 104146767 A | 11/2014 | |
| CN | 106308946 A | 1/2017 | |
| CN | 107414318 A | 12/2017 | |
| CN | 107961078 A | 4/2018 | |
| CN | 108366833 A | 8/2018 | |
| CN | 109421048 A | 3/2019 | |
| CN | 109549705 A | 4/2019 | |
| CN | 109998683 A | 7/2019 | |
| CN | 110370316 A | 10/2019 | |
| CN | 110458886 A | 11/2019 | |
| CN | 110897717 A | 3/2020 | |
| WO | WO-2015142802 A1 * | 9/2015 | ............. A61B 34/20 |

* cited by examiner

NAVIGATION SURGICAL SYSTEM, REGISTRATION METHOD THEREOF AND ELECTRONIC DEVICE

CROSS-REFERENCE TO RELATED APPLICATION

This application claims the priority of Chinese patent application number 201911252494.1, filed on Dec. 9, 2019, the entire contents of which are incorporated herein by reference.

TECHNICAL FIELD

The present invention relates to the field of robot-assisted navigation surgery, and in particular, to a navigation surgical system, a registration method thereof and an electronic device.

BACKGROUND

Navigation surgical systems are increasingly used in surgical procedures, especially in orthopedic surgeries. For example, the MAKO, the Robodoc, and other existing orthopedic navigation surgical systems all use a combination of robotic arm and infrared optical navigation device to assist a surgeon to conduct a surgical operation based on a pre-operative plan in combination with intra-operative registration technology. The intra-operative registration technology typically involves collecting real position information of the bone by using the optical navigation device, matching the real position information with the coordinate system of the skeletal model in the software, and using the robot to assist the surgeon with the surgery. In such surgical procedures, the registration technology is the key technology to link the robot and the navigation device. Based on the registration technology, the robot determines the position of the operation area and performs active position tracking or assists surgical operation according to the surgical plan. However, the existing registration tool and method have the following problems:

1) The procedure is cumbersome and causes extra operation time. Generally, before registering a bone, the robotic arm is first registered so as to register a relative position between the robotic arm and the navigation device. The conventional registration method of a robotic arm is conducted by installing a trackable element at a tail end of the robotic arm and removing the trackable element after the registration is completed. However, the installation requirement is high, and the connection between the robotic arm and the trackable element is usually a fixed connection, and thus the process of removing and installing the trackable element is time-consuming. Moreover, when performing bone registration, it is necessary to replace said trackable element with another type of trackable element. However, orthopedic surgeries generally require minimizing exposure time to the surgical area to reduce the probability of infection.

2) Poor reliability and poor real-time performance. Different from the foregoing, in another method of registering a robotic arm, the bone is first registered, and then the position of the end effector or a surgical instrument is tracked in real time by using a trackable element mounted on the base or the tail end of the robotic arm. However, vibration generates during the movement of the robotic arm, and thus the accuracy of the position of trackable element collected by the navigation device is affected by the vibration. Therefore, the registration accuracy of the robotic arm is low.

SUMMARY OF THE INVENTION

In order to solve the above technical problems, the present invention provides a navigation surgical system, a registration method thereof, and an electronic device, in order to simplify the surgical procedure, shorten the operation time, and improve the reliability and the real-time performance of position tracking.

According to an aspect of the present invention, a navigation surgical system provided by the present invention includes a robotic system and a navigation system communicatively connected to the robotic system; the robotic system includes a robotic arm, and the navigation system includes a navigation tracking device;

the robotic system has a robotic-arm based coordinate system established according to the robotic arm, and the robotic-arm based coordinate system is configured to be fixed relative to a supporting device;

the navigation system has a reference coordinate system that is recognizable by the navigation tracking device, and the reference coordinate system is configured to be fixed relative to the supporting device;

the navigation surgical system is configured to determine a relative position between the robotic arm and the navigation tracking device according to a relative position between the robotic-arm based coordinate system and the supporting device, and a relative position between the reference coordinate system and the supporting device.

Optionally, the navigation surgical system includes a robotic-arm fixing device, and the robotic arm is fixed on the supporting device by the robotic-arm fixing device; the robotic-arm fixing device includes a vertical frame and a horizontal cantilever; the frame has a first end fixed on the supporting device and a second end connected to a first end of the horizontal cantilever, and a second end of the horizontal cantilever is connected to the robotic arm.

Optionally, the robotic arm has a basal joint, the basal joint is fixed in position relative to the supporting device, and the robotic-arm based coordinate system is established according to the basal joint.

Optionally, the navigation surgical system is further configured to obtain the relative position between the robotic-arm based coordinate system and the the supporting device according to a length of the horizontal cantilever and a height of the horizontal cantilever relative to the supporting device.

Optionally, the navigation surgical system further includes a surgical trolley, and the robotic arm is mounted on the surgical trolley, and the surgical trolley is fixed in position relative to the supporting device; the robotic arm has a basal joint that is fixed in position relative to the surgical trolley, and the robotic-arm based coordinate system is established according to the basal joint.

Optionally, the reference coordinate system is established according to the supporting device or according to the surgical trolley.

Optionally, the navigation surgical system further includes a navigation trolley, and the navigation tracking device is mounted on the navigation trolley.

Optionally, the navigation surgical system further includes a navigation arm; the navigation tracking device is fixed on the supporting device by the navigation arm, and the navigation arm is provided with multiple of degrees of freedom to drive the navigation tracking device connected at an end of the navigation arm to move, and to adjust a position and a posture of the navigation tracking device.

Optionally, the navigation arm has a navigation basal joint, and the navigation basal joint is fixed in position relative to the supporting device, and the reference coordinate system is established according to the supporting device or according to the navigation basal joint.

Optionally, the navigation surgical system further includes a surgical-object fixing device for fixing a surgical object on the supporting device and fixing the surgical object in position relative to the supporting device; wherein the navigation system further includes a trackable element for marking a plurality of feature points on the surgical object, and the navigation surgical system is configured to obtain a position of a target area on the surgical object relative to the robotic arm according to the plurality of feature points.

Optionally, the navigation tracking device is an optical navigation tracking device, and the navigation system further includes a plurality of optical markers, each of which is recognizable by the optical navigation tracking device; the plurality of optical markers are configured to establish the reference coordinate system.

Optionally, at least three optical markers are provided on the supporting device.

Optionally, the optical marker is a spherical reflective marker or a sticker-type reflective marker.

Optionally, the navigation tracking device is a magnetic navigation tracking device, and the magnetic navigation tracking device includes a magnetic transmitting device and a magnetic positioning device, the magnetic transmitting device is configured to generate a magnetic field, and the magnetic positioning device is configured to generate an electrical signal induced by the magnetic field to establish the reference coordinate system.

Optionally, the magnetic positioning device includes an induction coil.

Optionally, the navigation tracking device is an inertial navigation tracking device, and the navigation system includes at least one inertial navigation marker that is recognizable by the inertial navigation tracking device for establishing the reference coordinate system.

Optionally, the inertial navigation marker is configured to be arranged on a surgical subject.

Optionally, a target is provided at an end of the robotic arm, and the target is configured to track a spatial position of the end of the robotic arm.

According to another aspect of the present invention, the registration method for a navigation surgical system provided by the present invention includes a robotic system and a navigation system communicatively connected to the robotic system, the robotic system includes a robotic arm, and the navigation system includes a navigation tracking device, the registration method includes:

establishing, in the navigation surgical system, a reference coordinate system that is recognizable by the navigation tracking device, wherein the reference coordinate system is fixed in position relative to a supporting device;

establishing a robotic-arm based coordinate system according to the robotic arm, wherein the robotic-arm based coordinate system is fixed in position relative to the supporting device; and determining a relative position between the navigation tracking device and the robotic arm according to a relative position between the robotic-arm based coordinate system and the supporting device, and a relative position between the reference coordinate system and the supporting device.

Optionally, the step of establishing the robotic-arm based coordinate system includes establishing the robotic-arm based coordinate system at a basal joint of the robotic arm, wherein the basal joint of the robotic arm is fixed in position relative to the supporting device.

Optionally, the step of establishing the reference coordinate system includes establishing the reference coordinate system according to a surgical trolley, according to the supporting device or according to a navigation basal joint of a navigation arm for fixing the navigation tracking device on the supporting device by the navigation arm, and making the surgical trolley or the navigation basal joint of the navigation arm fixed in position relative to the supporting device.

Optionally, the robotic arm is fixed on the supporting device by a robotic-arm fixing device, the robotic-arm fixing device including a vertical frame and a horizontal cantilever, the frame having a first end fixed to the supporting device and a second end connected to a first end of the cantilever, a second end of the cantilever being connected to the robotic arm, wherein a position of the robotic-arm based coordinate system relative to the the supporting device is determined according to a length of the cantilever and a height of the cantilever relative to the supporting device.

Optionally, the registration method further includes fixing the navigation tracking device on the supporting device by a navigation arm to adjust a position and a posture of the navigation tracking device by the navigation arm.

Optionally, the registration method further includes determining a position of a target area on a surgical object relative to the robotic arm according to a plurality of feature points provided on the surgical object, wherein the surgical object is fixed in position relative to the supporting device.

Optionally, the reference coordinate system is recognized and established by using an optical navigation tracking device, a magnetic navigation tracking device, or an inertial navigation tracking device.

According to another aspect of the present invention, the electronic device provided by the present invention includes a controller and a memory, and the memory stores a computer program, and the computer program is configured to execute the computer program by:

establishing, in a navigation surgical system, a reference coordinate system that is recognizable by a navigation tracking device, wherein the reference coordinate system is fixed in position relative to a supporting device;

establishing a robotic-arm based coordinate system according to a robotic arm, wherein the robotic-arm based coordinate system is fixed in position relative to the supporting device; and determining a relative position between the navigation tracking device and the robotic arm according to a relative position between the robotic-arm based coordinate system and the supporting device, and a relative position between the reference coordinate system and the supporting device.

In the navigation surgical system and the registration method thereof provided by the present invention, by fixing in position the robotic-arm based coordinate system relative to the supporting device, and fixing in position of the reference coordinate system that is recognizable by the navigation tracking device relative to the supporting device, it can directly register the relative position between the robotic arm and the navigation tracking device without the need to install a target at the end of the robotic arm or the base of the robotic arm to register the robotic arm, thereby simplifying the surgical process, shortening the exposure time of the surgical area, and reducing the chance of patients being infected. In particular, during the operation, since the target does not need to be mounted on the robotic arm, the acquisition of the end position of the robotic arm will not be affected by the vibration during the movement of the robotic arm. Therefore, the reliability and the real-time performance of the end position of the robotic arm are ensured.

BRIEF DESCRIPTION OF DRAWINGS

The implementation method of the present invention and the features, properties, and advantages of the related embodiments will be described by referring to the following drawings, in which.

DETAILED DESCRIPTION OF EXEMPLARY EMBODIMENTS

In the following, the technical solutions in the preferred embodiments of the present invention will be clearly and completely described with reference to the drawings in the embodiments of the present invention. Based on the embodiments of the present invention, all other embodiments obtained by those skilled in the art without creative efforts shall fall within the protection scope of the present invention.

As used in the present invention, the singular forms "a", "an" and "the" include plural referents unless the content clearly dictates otherwise. As used in the present invention, the term "or" is generally used in its sense including "and/or" unless the content clearly dictates otherwise. As used in the present invention, the term "several" is generally used in its sense including "at least one" unless the content clearly indicates otherwise. As used in the present invention, the term "at least two" is generally used in its sense including "two or more" unless the content clearly indicates otherwise. In addition, the terms "first", "second" and "third" are used for descriptive purposes only, and cannot be understood as indicating or implying relative importance or implicitly indicating the number of technical features indicated. Therefore, the features defined as "first", "second" and "third" may explicitly or implicitly include one or at least two of the features.

Figure 1:
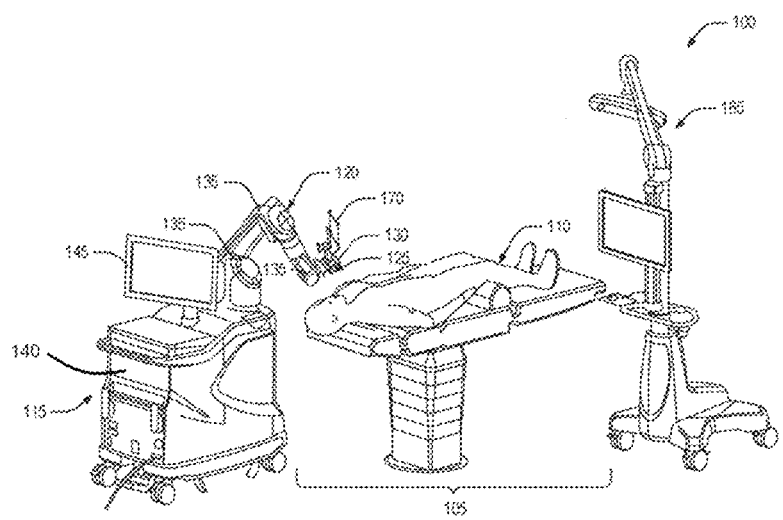
FIG. 1 is a schematic diagram of a conventional navigation surgical system.

As described in the background, the existing navigation surgical system has the problems of complicated registration process, long extra operation time, poor reliability and poor real-time performance of position tracking. To better understand these problems, please refer to FIG. 1, the conventional navigation surgical system 100 for operating on an operation area 105 of a patient 110, specifically includes a robotic system 115 and a navigation system 165. The robotic system 115 includes a robotic arm 120. During surgery, the robotic arm 120 is provided with an end effector or a surgical instrument 125 at its distal end 130. The surgical instrument 125 is positioned by the robotic arm 120.

The robotic arm 120 includes a plurality of joints 135 that allow the surgical instrument 125 to be positioned at any desired location near or inside a given surgical area 105. The robotic system 115 further includes a computer system for operating the robotic arm 120 and the surgical instrument 125. The computer system includes a controller located in the controlling trolley 140, and a human-machine interface device 145, such as a display, located on the controlling trolley 140 to provide the surgeon with images used during surgery. The computer system is in communication with a navigation system 165, the navigation system 165 is configured to monitor multiple tracking elements fixed to the object of interest, such as an optical target 170 at the end of the robotic arm, to track the positions of the multiple objects within the surgical area. The navigation system 165 is used to interact with the optical target 170 to establish a virtual three-dimensional coordinate system within the surgical area for tracking the patient's anatomy, the surgical instrument, or other part of the robotic system 115. The optical target 170 is placed on the robotic arm 120 or on the surgical instrument 125 to track the position of the virtual three-dimensional coordinate system, thereby providing positioning data, such as patient location, the position of the bone, joint position, the position of the robotic arm and the like. The robotic arm 120 is fixed on the controlling trolley 140.

During the surgery, the navigation system 165 tracks the spatial positions of the end of the robotic arm or surgical instrument in real time and displays the positions on the display. In order to achieve this purpose, it is common practice to mount a trackable element on the end of the robotic arm or on the base of the robotic arm, and track the target by the navigation system 165 to achieve real-time tracking of the end of the robotic arm/surgical instrument. However, in actual use, the vibration of the robotic arm will cause the trackable element on the robotic arm to vibrate, which will greatly affect the reliability and the real-time performance of tracking.

Based on this, the present invention provides a navigation surgical system and a registration method for the navigation surgical system, which can achieve the purpose of real-time tracking of the position of the end of the robotic arm by the navigation system without installing a trackable element on the end of the robotic arm or on the base of the robotic arm. It improves the reliability and the real-time performance of tracking of the end of the robotic arm, and also eliminates the registration process for the robotic arm, shortens the additional operation time, and reduces the chance of infection of the patient.

Specifically, the navigation surgical system provided by the present invention includes a robotic system system and a navigation system communicatively connected to the robotic system. The robotic system includes a robotic arm, and the navigation system includes a navigation tracking device. The navigation tracking device includes an optical navigation tracking device, a magnetic navigation tracking device, or an inertial navigation tracking device. The core idea of the registration of the navigation surgical system is to establish a reference coordinate system that is recognizable by the navigation tracking device in the navigation surgical system, and fix the reference coordinate system relative to a supporting device for supporting the patient, such as the relative position between the hospital beds. At the same time, the robotic-arm based coordinate system is established according to the robotic arm, and the relative position between the robotic-arm based coordinate system and the supporting device is fixed; and a relative position between the robotic arm and the navigation tracking device is determined according to a relative position between the robotic-arm based coordinate system and the supporting device, and a relative position between the reference coordinate system and the supporting device. In this way, the process of registering a robotic arm by installing a target, such as an optical retro-reflective target at the end or base of the robotic arm can be eliminated, and the process of assembling and disassembling the target can be eliminated, thereby saving the operation time. And during the surgery, as long as the robotic system sends the position of the robotic arm to the navigation system in real time, the purpose of the navigation system to track the spatial positions end of the robotic arm or surgical instrument in real time can be achieved and display them on the display.

In the following, the navigation surgical system of the present invention and the implementation manner of its registration are further described with reference to the drawings and several embodiments.

Embodiment 1

Figure 2:
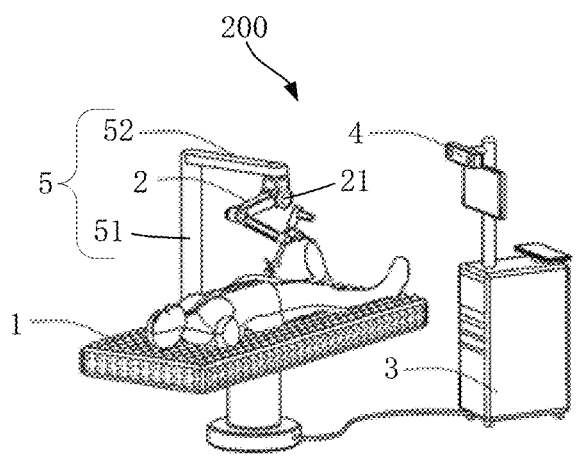
FIG. 2 is a schematic structural diagram of a navigation surgical system according to Embodiment 1 of the present invention.

FIG. 2 is a schematic structural diagram of a navigation surgical system 200 according to the first embodiment of the present invention. As shown in FIG. 2, this embodiment provides a navigation surgical system 200 including a robotic system and a navigation system communicatively connected to the robotic system. The robotic system includes a robotic arm 2, an end of the robotic arm 2 used to install a surgical instrument. The surgical instrument is designed as any surgical instrument suitable for use by the robotic system, such as a clamp, a flanging device, a reaming device or an impactor devices, or humeral head impactors, etc.

The navigation system includes an optical navigation tracking device 4 and a plurality of optical markers, the optical marker can be recognized and tracked by the optical navigation tracking device 4. In this embodiment, a plurality of the optical markers are mounted on a supporting device 1 (such as the hospital bed), and the positions of these optical markers relative to the supporting device 1 are fixed, decided and acquired. Therefore, in the navigation system of the present invention, based on a plurality of optical markers, a reference coordinate system can be established according to the supporting device 1, so that the position of the reference coordinate system relative to the supporting device 1 is fixed, decided and acquired. Further, a plurality of the optical markers are preferably distributed in a matrix on the supporting device 1 to simplify the calculation process. In some embodiments, a plurality of the optical markers are arranged on the supporting device 1 at a fixed pitch. Furthermore, the number of the optical markers is at least three, so that a space rectangular coordinate system is established according to the at least three optical markers, that is, the reference coordinate system is a space rectangular coordinate system. In this embodiment, the position of the optical marker on the supporting device is not limited, as long as the position of the optical marker on the supporting device 1 is fixed, and the installation position of the optical marker relative to the supporting device is also known before surgery. That is, the position of the reference coordinate system on the supporting device is decided and acquired. Further, the optical marker is a spherical reflective marker or a sticker reflective marker.

In this embodiment, the robotic arm 2 is fixed on the supporting device 1 by a robotic-arm fixing device 5, and the position of the robotic-arm fixing device 5 relative to the supporting device 1 is fixed and known, that is, the the position of the robotic-arm fixing device 5 relative to the supporting device 1 is fixed, decided and acquired. The robotic arm fixing device 5 specifically includes a vertical frame 51 and a horizontal cantilever 52. One end of the frame 51 is fixed to the supporting device 1, the other end of the frame 51 is connected to one end of the cantilever 52, and the other end of the cantilever 52 is connected to the robotic arm 2. In this embodiment, the robotic arm 2 has a base, and the base is fixed on the cantilever 52. The robotic arm 2 also has a basal joint 21 which is directly rotatably connected to the base. The invention does not limit the configuration of the robotic arm 2. For example, the robotic arm 2 comprises a plurality of rotary joints connected in series, and any two adjacent rotary joints are connected by a joint arm.

In this embodiment, the robotic system has a robotic-arm based coordinate system established according to robotic arm 2, the position of the robotic-arm based coordinate system relative to the supporting device 1 is fixed, that is, the position of the robotic-arm based coordinate system relative to the reference coordinate system remains fixed, decided and acquired before surgery. In this way, the registration of the relative position between the robotic arm 2 and the optical navigation tracking device 4 is achieved, so that the optical navigation tracking device 4 can track the position of the robotic arm in real time.

Further, the robotic-arm based coordinate system is preferably established according to a basal joint 21 of the robotic arm 2, and the position of the basal joint 21 of the robotic arm 2 relative to the supporting device 1 is fixed, decided and acquired. Further in this embodiment, the navigation surgical system 200 obtains the relative position between the basal joint 21 of the robotic arm 2 and the supporting device according to the length of the cantilever 52 and the height of the cantilever 52 relative to the supporting device 1, and the position robotic-arm based coordinate system relative to the supporting device is determined.

Compared with the traditional registration method of the robotic arm, the navigation surgical system 200 of the present invention can register the relative position between the robotic arm and the optical navigation tracking device without installing a target on the end of the robotic arm. The procedure, therefore, shortens the surgical time, reduces the exposure time of the surgical area, and reduces the chance of the patient being infected. In addition, with this registration method, the position of the robotic arm will not be affected by the vibration generated during the movement of the robotic arm in the process of operation. Therefore, the accuracy of the position of the robotic arm, the reliability and the real-time performance are improved, and thus the accuracy of the surgical operation is further improved. Furthermore, it is only necessary to perform bone registration, so that the optical navigation tracking device 4 obtains the position of the patient's bone relative to the supporting device 1. The optical navigation tracking device 4 sends the position information of the bone relative to the supporting device to the robotic system, and the robotic system obtains the position of the robotic arm 2 relative to the patient's bone according to the position information of the bone, and then the robotic arm 2 can be controlled to perform the osteotomy positioning operation. In this embodiment, the traditional registration methods can be used for bone registration. For example, a doctor holds a trackable element to select a registration point of interest on a patient's bone, and the optical navigation tracking device 4 obtains coordinate information of the bone registration point selected according to the trackable element, matches a real bone with a bone model in a navigation system, and feeds back the coordinate information to the controller, so that the controller can determine the position of the bone.

In some embodiments, an optical target is installed at the end of the robotic arm 2 to track the spatial position of the end of the robotic arm, so that redundant tracking of the position of the robotic arm is achieved, and the reliability of the surgical system is improved. In addition, the reference coordinate system is preferably disposed at a corner of the supporting device 1, so that the reference coordinate system prevents from being blocked by a doctor or a nurse, and the effectiveness of navigation is reliable.

The navigation surgical system 200 further includes a navigation trolley 3, and the optical navigation tracking device 4 is directly mounted on the navigation trolley 3. Further, the navigation system is communicatively connected with the robotic system via a cable. For example, the navigation system includes a navigation controller provided in the navigation trolley 3. The robotic system includes a robot controller provided at the bottom of the supporting device 1. The navigation controller and the robot controller communicated with each other via a cable. A display is provided on the navigation trolley 3 to display the position of the robotic arm or other information in real time.

It should be known that during the actual operation, the end of the robotic arm 2 needs to be connected with a surgical instrument. The surgical instrument includes, but is not limited to, a surgical instrument for joint surgery, a surgical instrument for spine surgery, or a surgery tool for brain. In the present invention, all the embodiments are described by taking a joint replacement surgical instrument as an example, but this should not be taken as a limitation on the present invention.

In summary, by applying the navigation surgical system 200 of this embodiment, only the robotic system, such as the position sensor of each joint, is required to feedback the position and the pose of the end of the robotic arm to the optical navigation tracking device 4 in real time. The optical navigation tracking device 4 obtain the spatial position of the end of the robotic arm and display it on the displayer, thereby achieving the purpose of tracking the position of the end instrument or surgical instrument in real time.

Embodiment 2

Figure 3:
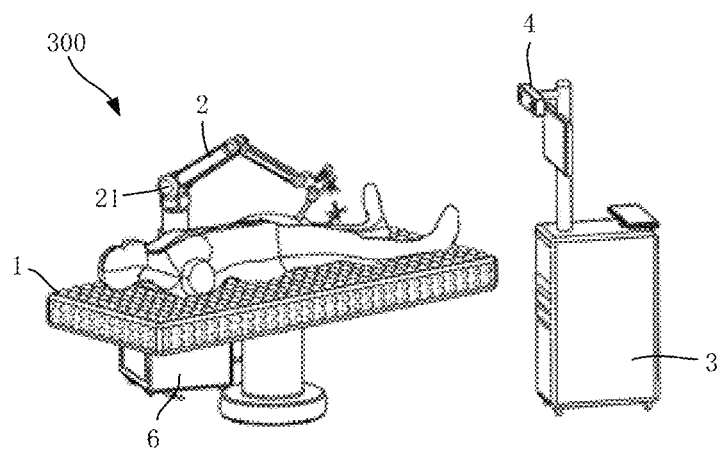
FIG. 3 is a schematic structural diagram of a navigation surgical system according to Embodiment 2 of the present invention along a first angle.
Figure 4:
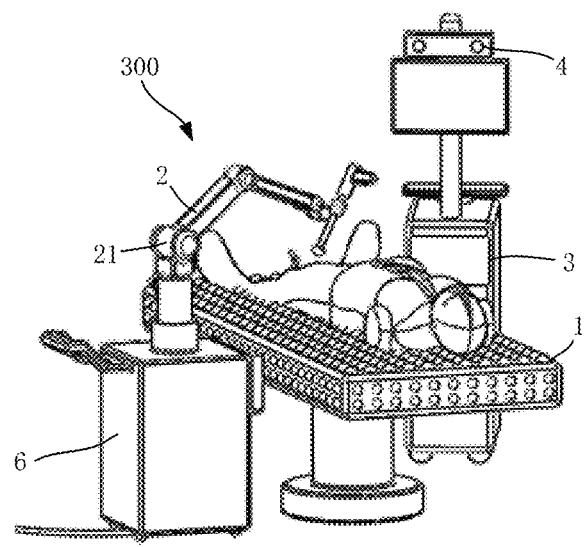
FIG. 4 is a schematic structural diagram of a navigation surgical system according to Embodiment 2 of the present invention along a second angle.

FIGS. 3 and 4 are schematic structural diagrams of a navigation surgical system 300 provided in Embodiment 2 of the present invention at different orientations, respectively. The structure of the navigation surgical system 300 provided in this embodiment is substantially the same as the structure of the navigation surgical system 200 of the first embodiment. The following mainly describes the differences between the two embodiments.

As shown in FIGS. 3 and 4, the navigation surgical system 300 of this embodiment further includes a surgical trolley 6, and the robotic arm 2 is directly fixed on the surgical trolley 6, and the position of the surgical trolley 6 relative to the supporting device 1 is fixed, decided and acquired. Based on the same principle, since the position of the basal joint 21 of the robotic arm 2 relative to the surgical trolley 1 is fixed, decided and acquired, the position of the robotic-arm based coordinate system relative to the supporting device 1 is also fixed, decided and acquired. Therefore, the relative position between the robotic-arm based coordinate system and the reference coordinate system is also decided and acquired.

Another difference is that the base of the robotic arm 2 in this embodiment is directly fixed on the surgical trolley 6, so that the robotic-arm fixing device 5 is eliminated. In addition, the robot controller is disposed in the surgical trolley 6 and communicates with the navigation controller in the navigation trolley 3 via a cable. In some embodiments, the robot controller and the navigation controller communicate wirelessly.

Embodiment 3

Figure 5:
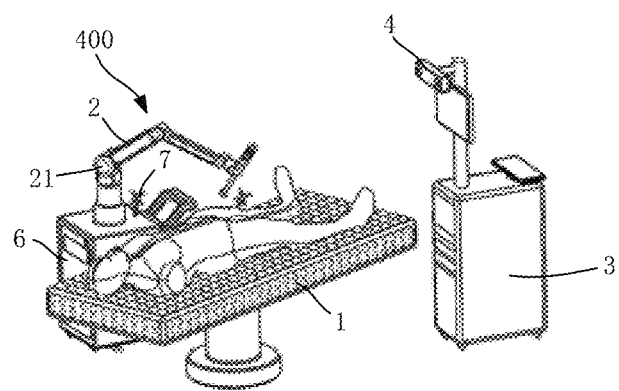
FIG. 5 is a schematic structural diagram of a navigation surgical system according to Embodiment 3 of the present invention.

FIG. 5 is a schematic structural diagram of a navigation surgical system 400 according to a third embodiment of the present invention. The structure of the navigation surgical system 400 provided in this embodiment is substantially the same as the structure of the navigation surgical system 300 of the second embodiment. The following mainly describes the differences between the two embodiments.

The reference coordinate system in this embodiment is not established according to the supporting device 1, but is established according to the surgical trolley 6. As shown in FIG. 5, an optical target 7 is provided on the surgical trolley 6. The optical target 7 has at least three reflective balls, which is convenient for establishing a reference coordinate system based on multiple reflective balls. Since the position of the surgical trolley 6 relative to the supporting device 1 is fixed, decided and acquired, the position of the reference coordinate system relative to the supporting device 1 is also fixed, decided and acquired. Similarly, since the relative position between the robotic-arm based coordinate system and the surgical trolley 6 is also fixed, decided and acquired, the relative position between the robotic-arm based coordinate system and the reference coordinate system is also fixed, decided and acquired, so that the relative position between the robotic arm 2 and the optical navigation tracking device 4 is also decided and acquired.

Embodiment 4

Figure 6:
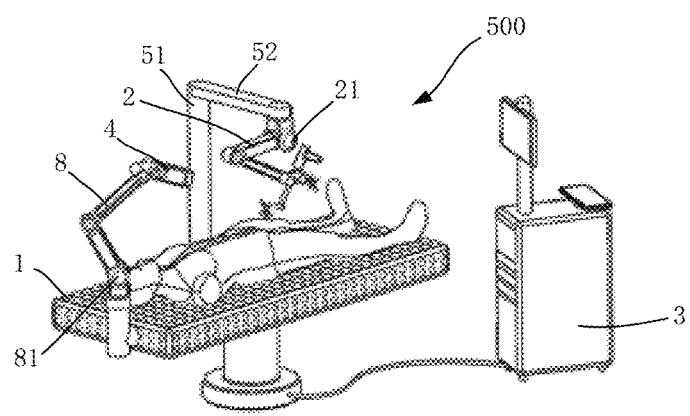
FIG. 6 is a schematic structural diagram of a navigation surgical system according to Embodiment 4 of the present invention.

FIG. 6 is a schematic structural diagram of a navigation surgical system 500 according to a fourth embodiment of the present invention. The structure of the navigation surgical system 500 provided in this embodiment is substantially the same as the structure of the navigation surgical system 200 in the first embodiment. The following mainly describes the differences between the two embodiments.

As shown in FIG. 6, the optical navigation tracking device 4 is fixed on the supporting device 1 by the navigation arm 8, so that it is convenient for the user to adjust the position and the posture of the optical navigation tracking device 4, which improves the operation efficiency, and the navigation trolley 3 can be far away from the supporting device 1 to increase the doctor's activity space. Specifically, the navigation arm 8 is also a robotic-arm configuration and has several degrees of freedom, and an optical navigation tracking device 4 is connected at an end of the navigation arm 8 to drive the optical navigation tracking device 4 to move, adjust the position and the posture of the optical navigation tracking device 4. In this embodiment, since the supporting device 1 is provided with an optical marker that can be recognized and tracked by the optical navigation tracking device 4, and the relative position between the robotic arm basal joint 21 and the supporting device 1 is fixed. Similarly, the relative position between the navigation basal joint 81 of the navigation arm 8 and the supporting device 1 is decided and acquired, so that the relative position between the robotic arm 2 and the optical navigation tracking device 4 is decided and acquired. No registration of the robotic arm is required, and only the bone registration is needed to obtain the position of the bone relative to the supporting device 1. The navigation system sends the position of the bone relative to the supporting device 1 to the robotic system, and then the robotic arm 2 performs the osteotomy positioning operation.

In addition, a navigation controller is still installed in the navigation trolley 3 in this embodiment and is connected to the robot controller at the bottom of the supporting device via a cable. In addition, the reference coordinate system can be established either according to the supporting device 1 or according to the navigation basal joint 81 of the navigation arm 8.

Embodiment 5

Figure 7:
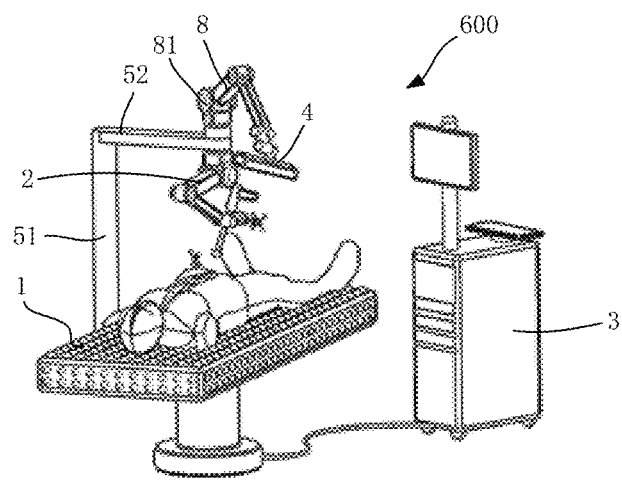
FIG. 7 is a schematic structural diagram of a navigation surgical system according to Embodiment 5 of the present invention.

FIG. 7 is a schematic structural diagram of a navigation surgical system 600 provided in Embodiment 5 of the present invention. The structure of the navigation surgical system 600 provided in this embodiment is substantially the same as that of the navigation surgical system 500 of the fourth embodiment, and the following mainly describes the differences between the two embodiments.

As shown in FIG. 7, the optical navigation tracking device 4 is fixed on the cantilever 52 by a navigation arm 8. In this embodiment, the robotic arm 2 is disposed below the cantilever 5, and the optical navigation tracking device 4 is disposed above the cantilever 5. In this manner, it is also convenient for the user to adjust the position and the posture of the optical navigation tracking device 4 to improve the operation efficiency, and the navigation trolley 3 can be far away from the supporting device 1 to increase the doctor's activity space.

Embodiment 6

Figure 8:
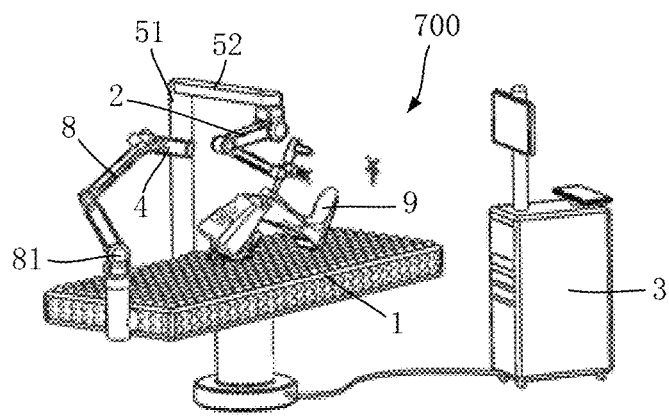
FIG. 8 is a schematic structural diagram of a navigation surgical system according to Embodiment 6 of the present invention.

FIG. 8 is a schematic structural diagram of a navigation surgical system 700 provided in Embodiment 6 of the present invention. The difference from the navigation surgical system 500 in the fourth embodiment is that the navigation surgical system 700 of this embodiment does not need to perform bone registration, and only needs to calibrate the position of the bone relative to the supporting device in advance.

Specifically, the navigation surgical system 700 of this embodiment also includes a surgical-object fixing device (not shown) for fixing a surgical object such as a patient's lower limb 9 on the supporting device 1 and fixing the position of the patient's lower limb 9 relative to the supporting device 1. In addition, the navigation system 700 further includes a trackable element for calibrating or mark a plurality of feature or selected points on the lower limb 9 of the patient, so that the navigation surgical system 700 obtains the position of the surgical area (i.e., a target area) on the lower limb of the patient relative to the robotic arm according to the plurality of feature points. Therefore, there is no need to install an additional optical target on the patient's lower limbs, which also saves the process of assembling and disassembling the additional optical target, further saving the operation time.

Figures 9A, 9B:
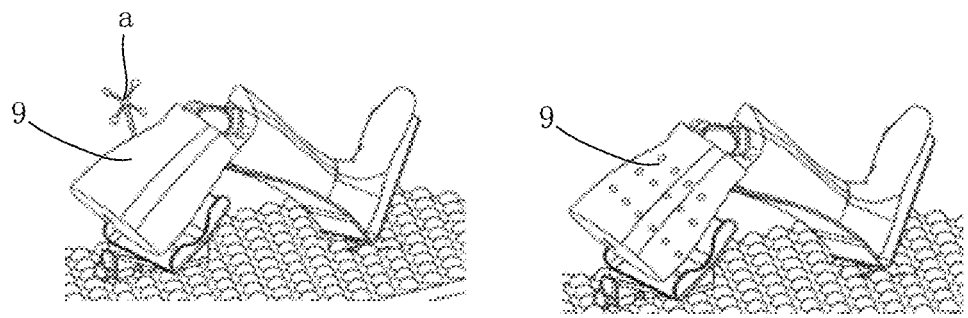
FIG. 9a is a schematic diagram of a traditional bone registration method.
FIG. 9b is a schematic diagram of a bone registration method according to the Embodiment 6 of the present invention.

For example, as shown in FIG. 9a, in the traditional bone registration process, a optical target a needs to be installed on the patient's lower limb 9 for bone registration. On the contrary, as shown in FIG. 9b, in this embodiment, there is no need to install a optical target on the lower limb 9 of the patient, and only a plurality of feature points need to be marked on the lower limb 9 of the patient to obtain a position of the robotic arm relative to the bone. The operation is more convenient, further reducing the additional surgical exposure time.

Embodiment 7

Figure 10:
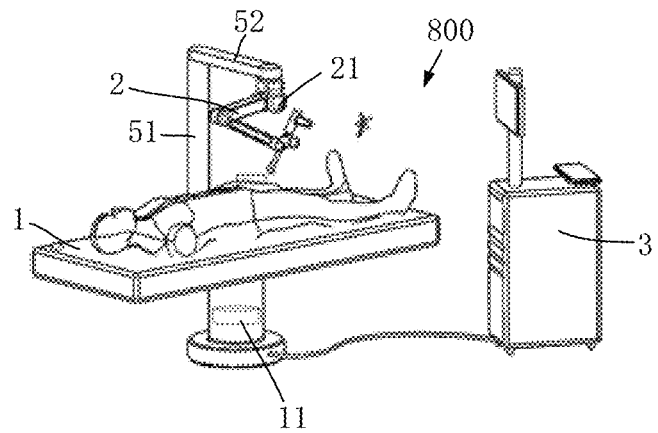
FIG. 10 is a schematic structural diagram of a navigation surgical system according to Embodiment 7 of the present invention.

FIG. 10 is a schematic structural diagram of a navigation surgical system 800 according to Embodiment 7 of the present invention. The structure of the navigation surgical system 800 provided in this embodiment is substantially the same as that of the navigation surgical system 200 in the first embodiment, and the following mainly describes the differences between the two embodiments.

In this embodiment, the optical navigation tracking device 4 is replaced by a magnetic navigation tracking device 11. Further, the magnetic navigation tracking device 11 includes a magnetic transmitting device and a magnetic positioning device. The magnetic transmitting device is configured to generate a magnetic field. The magnetic positioning device is configured to induce a magnetic field and generate an electrical signal (such as a voltage or current signal) induced by the magnetic field. Therefore, the navigation system establishes a reference coordinate system according to the electrical signal of the magnetic positioning device. In this embodiment, the magnetic transmitting device is arranged on the bottom of the supporting device 1, and at the same time, the optical marker on the supporting device is replaced by at least one magnetic positioning device (not shown). That is, a reference coordinate system is established according to the supporting device by a magnetic positioning device. Further, the magnetic positioning device includes at least one induction coil. Similarly, since the magnetic positioning device is recognizable by the magnetic navigation tracking device 11 and the position of the robotic arm relative to the supporting device 1 is fixed, decided and acquired, the position of the robotic arm relative to the magnetic navigation tracking device 11 is also decided and acquired. Compared with the optical navigation tracking device, this mode is not affected by the failure of the doctor or nurse to block the optical navigation tracking device during the operation, which leads to the failure of the navigation, and thus improves the reliability of the navigation surgery system.

Embodiment 8

Figure 11:
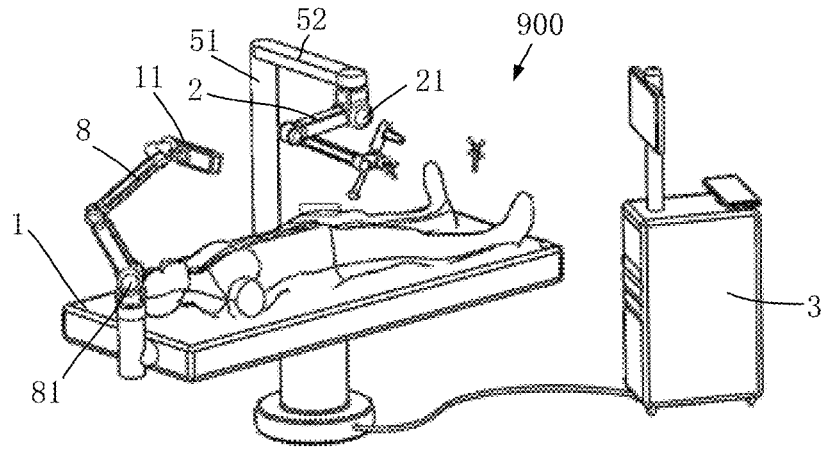
FIG. 11 is a schematic structural diagram of a navigation surgical system according to Embodiment 8 of the present invention.

FIG. 11 is a schematic structural diagram of a navigation surgical system 900 according to an eighth embodiment of the present invention. The structure of the navigation surgical system 900 provided in this embodiment is substantially the same as that of the navigation surgical system 800 of the seventh embodiment, and the following mainly describes the differences between the two embodiments.

As shown in FIG. 11, the magnetic navigation tracking device 11 is fixed on the supporting device 1 by a navigation arm 8, and the position of the navigation basal joint 81 of the navigation arm 8 relative to the supporting device 1 is fixed, decided and acquired. In addition, the magnetic positioning device is provided on the supporting device 1 or on the navigation basal joint 81 of the navigation arm 8, or at the basal joint 21 of the robotic arm 2.

Embodiment 9

Figure 12:
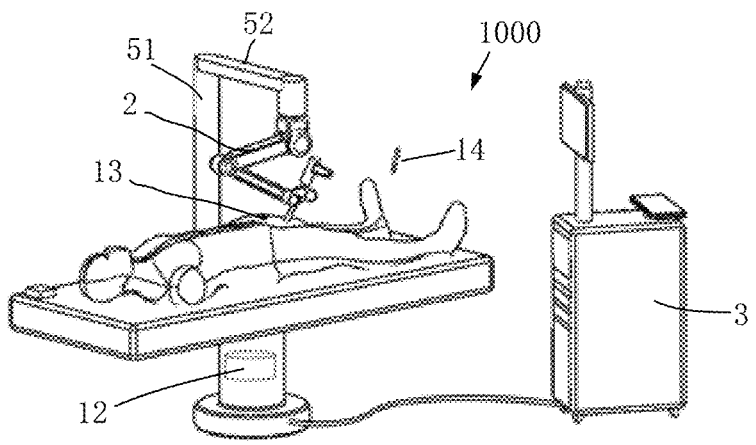
FIG. 12 is a schematic structural diagram of a navigation surgical system according to Embodiment 9 of the present invention.

FIG. 12 is a schematic structural diagram of a navigation surgical system 1000 provided in Embodiment 9 of the present invention. The structure of the navigation surgical system 1000 provided in this embodiment is substantially the same as the structure of the navigation surgical system 200 of the first embodiment. The following mainly describes the differences between the two embodiments.

As shown in FIG. 12, the optical navigation tracking device 4 is replaced by the inertial navigation tracking device 12. Further, the inertial navigation tracking device 12 includes an inertial navigation information processing unit (equivalent to a receiver), which can be placed on the bottom of the supporting device. At the same time, the navigation system also includes at least one inertial navigation marker 13. The inertial navigation marker 13 is recognizable by the inertial navigation information processing unit, that is, the position of the inertial navigation marker 13 relative to the supporting device 1 is acquired, decided and fixed. The position of the inertial navigation marker 13 is not limited in this embodiment, and for example is established according to the lower limb 9 of the patient. Therefore, the navigation system can establish a reference coordinate system according to the inertial navigation marker 13.

Compared with optical navigation tracking equipment, the use of inertial navigation tracking equipment prevents the navigation tracking equipment from being blocked by doctors or nurses during surgery, thereby avoiding the problem of navigation failure. In addition, during the actual surgery, the doctor can complete the bone registration by the inertial trackable element 14. In addition, the inertial navigation information processing unit is communicatively connected to the inertial navigation marker 13 via a cable, and the inertial navigation information processing unit is communicatively connected with the navigation controller in the navigation trolley 3 via a cable.

Figure 13:
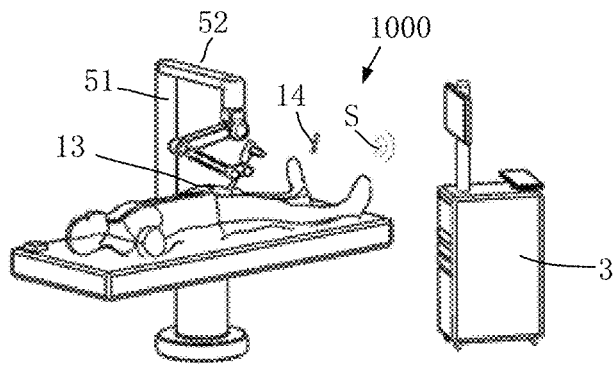
FIG. 13 is a schematic structural diagram of a navigation surgical system according to Embodiment 10 of the present invention.

In other embodiments, as shown in FIG. 13, the inertial navigation information processing unit is further provided in the navigation trolley 3, and the inertial navigation marker 13 is wirelessly connected with the inertial navigation information processing unit, such as wireless transmission through Bluetooth S.

In each of the above embodiments, the markers on the supporting device are not limited to optical reflective markers, magnetic positioning devices, inertial navigation markers, but also other ways that can be detected by the navigation tracking device, which is not limited in the present invention. In addition, the number and the arrangement of the optical markers on the supporting device are not limited, as long as at least part of the markers are not blocked by patients, doctors, nurses, etc. at any time during the surgery, they can be collected by the navigation tracking device.

An embodiment of the present invention further provides an electronic device including a controller and a memory. The memory stores a computer program. When the computer program is executed by the controller, the registration method described in FIG. 14 is performed.

Figure 14:
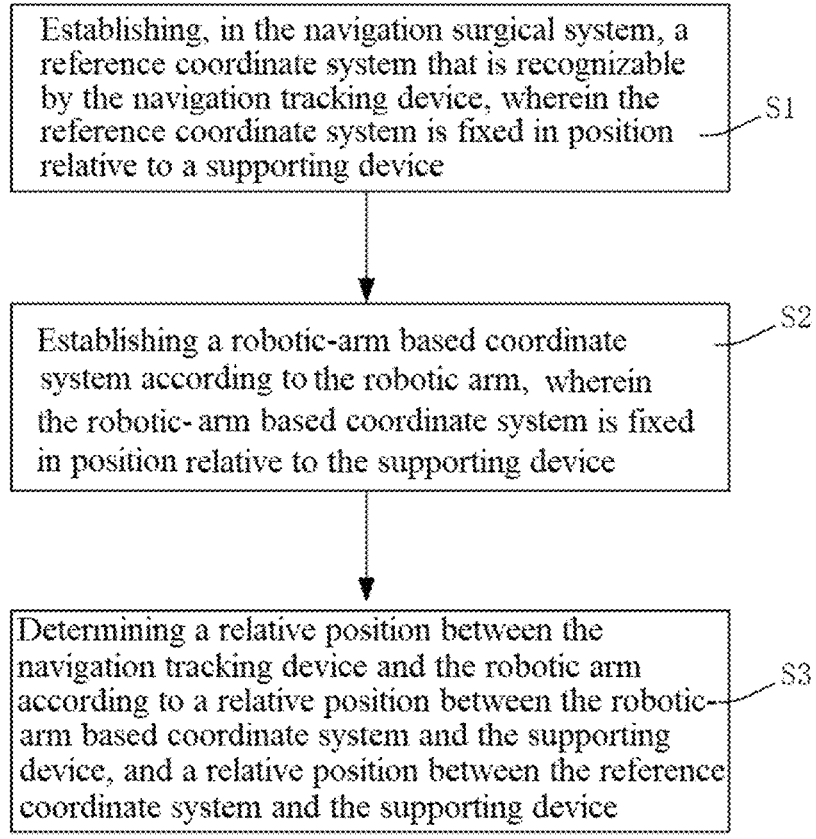
FIG. 14 is a registration flowchart of a navigation surgical system according to an embodiment of the present invention.

As shown in FIG. 14, an embodiment of the present invention further provides a registration method for a navigation surgical system, the registration method includes:

Step S1: establishing, in the navigation surgical system, a reference coordinate system that is recognizable by the navigation tracking device, wherein the reference coordinate system is fixed in position relative to a supporting device;

Step S2: establishing a robotic-arm based coordinate system according to the robotic arm, wherein the robotic-arm based coordinate system is fixed in position relative to the supporting device; and Step S3: determining a relative position between the navigation tracking device and the robotic arm according to a relative position between the robotic-arm based coordinate system and the supporting device, and a relative position between the reference coordinate system and the supporting device.

Further, establishing the robotic-arm based coordinate system includes establishing the robotic-arm based coordinate system according to a basal joint of the robotic arm, wherein the basal joint of the robotic arm is fixed in position relative to the supporting device.

Further, establishing the reference coordinate system includes establishing the reference coordinate system according to a surgical trolley, on the supporting device or on a navigation basal joint of a navigation arm for fixing the navigation tracking device on the supporting device by the navigation arm, and making the surgical trolley or the navigation basal joint of the navigation arm fixed in position relative to the supporting device.

Further, the registration method includes fixing the navigation tracking device on the supporting device by a navigation arm to adjust a position and a posture of the navigation tracking device by the navigation arm.

Further, the registration method includes determining a position of a target area on a surgical object relative to the robotic arm according to a plurality of feature points provided on the surgical object, wherein the surgical object is fixed in position relative to the supporting device.

In summary, the navigation surgical system according to the preferred embodiment of the present invention, by calibrating the relative position between the robotic-arm based coordinate system and the reference coordinate system that can be recognized by the navigation tracking device, the position registration between the robotic arm and the navigation tracking device can be achieved directly, without registering the robotic arm by installing an optical target. Therefore, the registration process of the robotic arm is eliminated, the operation time is shortened, and the risk of the patient being infected due to prolonged exposure to the operation area is reduced. During the surgery, because the optical target does not need to be installed on the robotic arm, the position acquisition of the end of the robotic arm will be not affected by the vibration during the movement of the robotic arm. Therefore, the position acquisition of the end of the robotic arm is reliable and real-time, and the accuracy of the position acquisition is improved.

The above description is only a description of the preferred embodiments of the present invention, and does not limit the scope of the present invention. Any changes and modifications made by a person of ordinary skill in the art according to the above disclosure shall fall within the protection scope of the present invention.

What is claimed is:

1. A navigation surgical system, comprising a robotic system and a navigation system communicatively connected to the robotic system, the robotic system comprising a robotic arm, the navigation system comprising a navigation tracking device,
   wherein the robotic system has a robotic-arm based coordinate system established according to the robotic arm, and the robotic-arm based coordinate system is configured to be fixed relative to a supporting device;
   wherein the navigation system has a reference coordinate system that is recognizable by the navigation tracking device, and the reference coordinate system is configured to be fixed relative to the supporting device;
   wherein the navigation surgical system is configured to determine a relative position between the robotic arm and the navigation tracking device according to a relative position between the robotic-arm based coordinate system and the supporting device, and a relative position between the reference coordinate system and the supporting device without need to install a target on the robotic arm for registering the robotic arm; and
   the navigation surgical system further comprising a robotic-arm fixing device, wherein the robotic arm is fixed on the supporting device by the robotic-arm fixing device; wherein the robotic-arm fixing device comprises a vertical frame and a horizontal cantilever; and wherein the frame has a first end fixed on the supporting device and a second end connected to a first end of the horizontal cantilever, and a second end of the horizontal cantilever is connected to the robotic arm.

2. The navigation surgical system of claim 1, wherein the robotic arm has a basal joint, and the basal joint is fixed in position relative to the supporting device, and wherein the robotic-arm based coordinate system is established according to the basal joint.

3. The navigation surgical system of claim 2, wherein the navigation surgical system is configured to obtain the relative position between the robotic-arm based coordinate system and the the supporting device according to a length of the horizontal cantilever and a height of the horizontal cantilever relative to the supporting device.

4. The navigation surgical system of claim 1, further comprising a surgical trolley, wherein the robotic arm is mounted on the surgical trolley, and the surgical trolley is fixed in position relative to the supporting device; wherein the robotic arm has a basal joint that is fixed in position relative to the surgical trolley, and the robotic-arm based coordinate system is established according to the basal joint; and wherein the reference coordinate system is established according to the supporting device or according to the surgical trolley.

5. The navigation surgical system of claim 1, further comprising a navigation arm, wherein the navigation tracking device is fixed on the supporting device by the navigation arm, and the navigation arm is provided with multiple of degrees of freedom to drive the navigation tracking device connected at an end of the navigation arm to move, and to adjust a position and a posture of the navigation tracking device.

6. The navigation surgical system of claim 5, wherein the navigation arm has a navigation basal joint, and the navigation basal joint is fixed in position relative to the supporting device; and wherein the reference coordinate system is established according to the supporting device or at the navigation basal joint.

7. The navigation surgical system of claim 1, further comprising a surgical-object fixing device for fixing a surgical object on the supporting device and fixing the surgical object in position relative to the supporting device; wherein the navigation system further comprises a trackable element for marking a plurality of feature points on the surgical object, and the navigation surgical system is configured to obtain a position of a target area on the surgical object relative to the robotic arm according to the plurality of feature points.

8. The navigation surgical system of claim 1, wherein the navigation tracking device is an optical navigation tracking device, the navigation system further comprising a plurality of optical markers, each of the plurality of optical markers being recognizable by the optical navigation tracking device; and wherein the plurality of optical markers are configured to establish the reference coordinate system.

9. The navigation surgical system of claim 8, wherein at least three optical markers are arranged on the supporting device, and/or
   wherein each of the plurality of optical markers is a spherical reflective marker or a sticker-type reflective marker.

10. The navigation surgical system of claim 1, wherein the navigation tracking device is a magnetic navigation tracking device comprising a magnetic transmitting device and a magnetic positioning device, the magnetic transmitting device configured to generate a magnetic field, the magnetic positioning device configured to generate an electrical signal induced by the magnetic field to establish the reference coordinate system.

11. The navigation surgical system of claim 1, wherein the navigation tracking device is an inertial navigation tracking device, the navigation system comprising at least one inertial navigation marker that is arranged on a surgical object and identifiable by the inertial navigation tracking device for establishing the reference coordinate system.

12. A registration method for a navigation surgical system, the navigation surgical system comprising a robotic system and a navigation system communicatively connected to the robotic system, the robotic system comprising a robotic arm, the navigation system comprising a navigation tracking device, wherein the registration method comprises:
   establishing, in the navigation surgical system, a reference coordinate system that is recognizable by the navigation tracking device, wherein the reference coordinate system is fixed in position relative to a supporting device;
   establishing a robotic-arm based coordinate system according to the robotic arm, wherein the robotic-arm based coordinate system is fixed in position relative to the supporting device; and
   determining a relative position between the navigation tracking device and the robotic arm according to a relative position between the robotic-arm based coordinate system and the supporting device, and a relative position between the reference coordinate system and the supporting device without need to install a target on the robotic arm for registering the robotic arm, wherein the step of establishing the robotic-arm based coordinate system comprises establishing the robotic-arm based coordinate system according to a basal joint of the robotic arm, wherein the basal joint of the robotic arm is fixed in position relative to the supporting device, wherein the step of establishing the reference coordinate system comprises establishing the reference coordinate system according to a surgical trolley, according to the supporting device or according to a navigation basal joint of a navigation arm for fixing the navigation tracking device on the supporting device by the navigation arm, and making the surgical trolley or the navigation basal joint of the navigation arm fixed in position relative to the supporting device, wherein the robotic arm is fixed on the supporting device by a robotic-arm fixing device, the robotic-arm fixing device comprising a vertical frame and a horizontal cantilever, the frame having a first end fixed to the supporting device and a second end connected to a first end of the cantilever, a second end of the cantilever being connected to the robotic arm, wherein a position of the robotic-arm based coordinate system relative to the the supporting device is determined according to a length of the cantilever and a height of the cantilever relative to the supporting device.

13. The registration method of claim 12, further comprising fixing the navigation tracking device on the supporting device by a navigation arm to adjust a position and a posture of the navigation tracking device by the navigation arm.

14. The registration method of claim 12, further comprising determining a position of a target area on a surgical object relative to the robotic arm according to a plurality of feature points provided on the surgical object, wherein the surgical object is fixed in position relative to the supporting device.

* * * * *